US008765123B1

(12) United States Patent
Kaplan

(10) Patent No.: US 8,765,123 B1
(45) Date of Patent: Jul. 1, 2014

(54) **COMPOSITIONS AND METHODS FOR THE TREATMENT AND PREVENTION OF INFECTIONS CAUSED BY *STAPHYLOCOCCUS AUREUS* BACTERIA**

(75) Inventor: Jeffrey B. Kaplan, Monsey, NY (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 0 days.

(21) Appl. No.: 13/609,714

(22) Filed: Sep. 11, 2012

Related U.S. Application Data

(63) Continuation of application No. 12/288,198, filed on Oct. 17, 2008, now abandoned.

(60) Provisional application No. 60/994,471, filed on Oct. 18, 2007.

(51) Int. Cl.
*A61K 38/47* (2006.01)

(52) U.S. Cl.
USPC .......................................... 424/94.61; 424/61

(58) Field of Classification Search
None
See application file for complete search history.

(56) References Cited

U.S. PATENT DOCUMENTS

| | | | | |
|---|---|---|---|---|
| 6,039,992 | A | 3/2000 | Compadre et al. | 426/332 |
| 2009/0191254 | A1* | 7/2009 | Curtin et al. | 424/423 |

OTHER PUBLICATIONS

Raad et al., Antimicrob. Agents Chemother., 2007, vol. 51, No. 1, p. 78-83, Abstract Only.*
Russell, A.D., Lancet 2003, vol. 3, p. 794-803.*
Akiyama et al. "*Staphylococcus aureus* Infection on Cut Wounds in the Mouse Skin: Experimental Staphylococcal Botryomycosis" Journal of Dermatological Science 1996 11:234-238.
Bal, A.M. and Gould, I.M. "Antibiotic Resistance in *Staphylococcus aureus* and its Relevance in Therapy" Expert Opinion on Pharmacotherapy 2005 6:2257-2269.
Bertino, J.S. "Intranasal Mupirocin for Outbreaks of Methicillian-Resistant *Staphylococcus aureus*" American Journal of Health-Systems Pharmacy 1997 54:2185-2191.
Buxton et al. "In Vivo Glycocalyx Expression by *Staphylococcus aureus* Phage Type 52/52A/80 in *S. aureus* Osteomyelitis" Journal of Infectious Disease 156(6):942-946.
Centers for Disease Control and Prevention "Reduced Susceptibility of *Staphylococcus aureus* to Vancomycin—Japan, 1996" Morbidity and Mortality Weekly Report 1997 46:624-626.
Eckhart et al. "DNase1L2 Suppresses Biofilm Formation by *Pseudomonas aeruginosa* and *Staphylococcus aureus*" British Journal of Dermatology 2007 156:1342-1345.
Fux et al. "Survival Strategies of Infectious Biofilms" Trends in Microbiology 2005 13(1):34-40.
Götz, F. "*Staphylococcus* and Biofilms" Molecular Microbiology 2002 43(6):1367-1378.
Horsburgh et al. "$\sigma^B$ Modulates Virulence Determinant Expression and Stress Resistance: Characterization of Functional rsbU Strain Derived from *Staphylococcus aureus* 8325-4" Journal of Bacteriology 2002 184(19):5457-5467.
Hurdle et al. "In vivo Transfer of High-Level Mupirocin Resistance from *Staphylococcus epidermidis* to Methicillin-Resistant *Staphylococcus aureus* Associated with Failure of Mupirocin Prophylaxis" Journal of Antimicrobial Chemotherapy 2005 56:1166-1168.
Izano et al. "Poly-N-acetylglucosamine Mediates Biofilm Formation and Detergent Resistance in *Aggregatibacter actinomycetemcomitans*" Microbial Pathogenesis 2007 44:52-60.
Kallen et al. "Perioperative Intranasal Mupirocin for the Prevention of Surgical-Site Infections: Systematic Review of the Literature and Meta-Analysis" Infection Control and Hospital Epidemiology 2005 26(12):916-922.
Kaplan, J.B. and Fine, D.H. "Biofilm Dispersal of *Neisseria subflava* and Other Phylogenetically Diverse Oral Bacteria" Applied and Environmental Microbiology 2002 68(10):4943-4950.
Kresken et al. "Prevalence of Mupirocin Resistance in Clinical Isolates of *Staphylococcus aureus* and *Staphylococcus epidermidis*: Results of the Antimicrobial Resistance Surveillance Study of the Paul-Ehrlich-Society for Chemotherapy, 2001" International Journal of Antimicrobial Agents 2004 23:577-581.
Lodise, T.P. and McKinnon, P.S. "Burden of Methicillin-Resistant *Staphylococcus aureus*: Focus on Clinical and Economic Outcomes" Pharmacotherapy 2007 27:1001-1012.
Lowry, F.D. "*Staphylococcus aureus* Infections" New England Journal of Medicine 1998 339:520-532.
O'Toole, G.A. and Kolter, R. Initiation of Biofilm Formation in *Pseudomonas fluorescens* WCS365 Proceeds via Multiple, Convergent Signaling Pathways: a Genetic Analysis 1998 28(3):449-461.
Otto, M. "*Staphylococcus* Biofilms" Current Topics in Microbiology and Immunology 2008 322:207-228.
Pope, S.D. and Roecker, A.M. "Vancomycin for Treatment of Invasive, Multi-Drug Resistant *Staphylococcus aureus* Infections" Expert Opinion on Pharmacotherapy 2007 8:1245-1261.
Sack, K. "Swabs in Hand, Hospital Cuts Deadly Infections" New York Times, Jul. 27, 2007, p. 1.
Stevens, D.L. "Community-Acquired *Staphylococcus aureus* Infections: Increasing Virulence and Emerging Methicillin Resistance in the New Millennium" Current Opinion in Infectious Diseases 2003 16:189-191.
Tristan et al. "Virulence Determinants in Community and Hospital Meticillin-Resistant *Staphylococcus aureus*" Journal of Hospital Infection 2007 65(S2):105-109.

(Continued)

*Primary Examiner* — Kade Ariani
(74) *Attorney, Agent, or Firm* — Licata & Tyrrell P.C.

(57) ABSTRACT

The present invention relates to antimicrobial deoxyribonuclease-based compositions that inhibit growth and proliferation of *Staphylococcus aureus* bacteria. The present invention also relates to methods of administering the compositions in the treatment and prevention of *S. aureus* infections. The present invention also relates to methods of administering the compositions in the eradication of *S. aureus* nasal carriage, in order to prevent the transmission of *S. aureus* bacteria.

9 Claims, 9 Drawing Sheets

(56) References Cited

OTHER PUBLICATIONS

Whitener et al. "Vacomycin-Resistant *Staphylococcus aureus* in the Absence of Vacomycin Exposure" Clinical Infectious Diseases 2004 38:1049-1055.

Office Communication dated Aug. 3, 2011 from U.S. Appl. No. 12/288,198, filed Oct. 17, 2008.
Office Communication dated Jan. 18, 2012 from U.S. Appl. No. 12/288,198, filed Oct. 17, 2008.

* cited by examiner

COMPOSITIONS AND METHODS FOR THE TREATMENT AND PREVENTION OF INFECTIONS CAUSED BY *STAPHYLOCOCCUS AUREUS* BACTERIA

This patent application is a continuation of U.S. application Ser. No. 12/288,198, filed Oct. 17, 2008 now abandoned, which claims the benefit of priority from U.S. Provisional application No. 60/994,471, filed Oct. 18, 2007, teachings of each of which are herein incorporated by reference in their entireties.

This invention was made with government support under Grant No. 5R01DE015124 awarded by National Institutes of Health. The government has certain rights in the invention.

FIELD OF THE INVENTION

The present invention relates to antimicrobial deoxyribonuclease-based compositions that inhibit growth and proliferation of *Staphylococcus aureus* bacteria. The present invention also relates to methods of administering the compositions in the treatment and prevention of *S. aureus* infections. The present invention also relates to methods of administering the compositions in the eradication of *S. aureus* nasal carriage, in order to prevent the transmission of *S. aureus* bacteria.

BACKGROUND

The Gram-positive bacterium *Staphylococcus aureus* is a major human pathogen (Lowy, 1998. New Engl. J. Med. 339:520-532). *S. aureus* causes numerous infections including acute skin abscesses (pimples, boils, styes, furunculosis) and invasive infections (pneumonia, mastitis, phlebitis, meningitis, urinary tract infections, osteomyelitis), as well as life-threatening bacteremias and endocarditis. *S. aureus* is a major pathogen in nosocomial infections, and in infections in patients with indwelling medical devices. *S. aureus* is also a major pathogen in infections of wounds, including infected diabetic foot ulcers, as well as in burn wounds. *S. aureus* can also cause toxin-mediated infections including food poisoning and toxic shock syndrome. Over the past 20 years, the frequencies of both nosocomial and community-acquired *S. aureus* infections has been steadily increasing (Stevens, 2003. Curr. Opin. Infect. Dis. 16:189-191). In addition, numerous multidrug-resistant strains of *S. aureus* have emerged in recent years (Bal & Gould, 2005. Expert Opin. Pharmacother. 6:2257-2269). These include methicillin-resistant *S. aureus* (MRSA), which are resistant to all penicillinase-resistant penicillins and cephalosporins (Lowy, 1998. New Engl. J. Med. 339:520-532). Infections caused by MRSA are commonly treated with vancomycin (Pope & Roecker, 2007. Expert Opin. Pharmacother. 8:1245-1261). Recently, however, vancomycin-resistant *S. aureus* (VRSA) strains have been isolated (Whitener et al., 2004. Clin. Infect. Dis. 38:1049-1055). In addition, *S. aureus* strains that exhibit resistance to intermediate levels of vancomycin (vancomycin-intermediate *S. aureus* or VISA) have been isolated (Centers for Disease Control and Prevention, 1997. MMWR Morb. Mortal. Wkly. Rep. 46:624-626). The percentage of *S. aureus* infections caused by MRSA, VRSA and VISA strains has been increasing (Lodise & McKinnon, 2007. Pharmacother. 27:2002-2012). Infections caused by MRSA, VRSA and VISA strains are often more severe, more easily transmitted, and more difficult to treat, than are infection caused by methicillin-sensitive *S. aureus* (MSSA) strains (Tristan et al., 2007. J. Hosp. Infect. 65 Suppl 2:105-109). Also, multidrug-resistance may eventually lead to the evolution of *S. aureus* strains that are resistant to all known antibiotics. New methods for treating and preventing *S. aureus* infections are urgently needed.

*S. aureus* is the leading cause of hospital-acquired infections. The federal Centers for Disease Control and Prevention estimates that in 2006 one in 22 hospitalized patients will experience a hospital-acquired infection, resulting in a total of 1.7 million infections and 99,000 deaths (Sack, 2007. New York Times July 27, p. 1). These nosocomial infections account for a significant portion of healthcare expenditures in the United States (Lodise & McKinnon, 2007. Pharmacother. 27:2002-2012). People who are at a higher risk for *S. aureus* infections include hospitalized patients, older patients, patients with type 1 diabetes, intravenous drug users, patients undergoing hemodialysis, surgical patients, HIV patients, patients with intravascular devices, patients with prosthetic heart valves, patients taking immunosuppressive drugs, and patients with defective leukocyte function. The large number of susceptible patients and the high number of nosocomial infections and deaths underscores the need for improved methods for treating and preventing *S. aureus* infections.

*S. aureus* is a natural commensal bacterium that colonizes the anterior nares of approximately 30 to 50 percent of healthy adults. Infection results when a breach in the mucosal barrier or skin allows bacterial cells access to the underlying tissues or to the bloodstream (Lowy, 1998. New Engl. J. Med. 339:520-532). Sites of infection are usually colonized by bacteria from the patient's own nasal reservoir, from contact with an infected patient, or from exposure to the transiently-colonized hands of healthcare workers. Previous studies have shown that eradication of *S. aureus* nasal carriage results in a decrease in the rate of *S. aureus* nosocomial infections (Kallen et al., 2005. Infect. Control Hosp. Epidemiol. 26:916-922). Mupirocin cream, applied topically to the nares, has been shown to effectively reduce *S. aureus* nasal carriage (Bertino, 1997. Amer. J. Health Systems Pharm. 54:2185-2191). However, mupirocin cream needs to be administered 3 times per day for 5 days, and mupirocin-resistant MSSA and MRSA strains have been identified (Kresken et al., 2004. Int. J. Antimicrob. Agents 23:577-581; Hurdle et al., 2005. J. Antimicrob. Chemother. 56:1166-1168). Therefore, there is a need for a method for eradicating *S. aureus* nasal carriage that is more efficient and less susceptible to the evolution of antimicrobial resistance.

*S. aureus* is known for its ability to form biofilms, which are defined as communities of bacteria, encased in a self-synthesized extracellular polymeric matrix, growing attached to a biotic or abiotic surface (Gotz, 2002. Mol. Microbiol. 43:1367-1378). Evidence suggests that biofilm formation plays a role in *S. aureus* wound infections (Akiyama et al., 1996. J. Dermatol. Sci. 11:234-238) and osteomyelitis (Buxton et al., 1987. J. Infect. Dis. 156:942-946). Biofilm formation may also play a role in other localized *S. aureus* infections. Biofilms that form on tissues or medical devices are extremely difficult to eradicate because the biofilm mode of growth protects bacterial cells from killing by antibiotics and host defenses (Fux et al., 2005. Trends Microbiol. 13:34-40). Therefore, there is a need for anti-infective therapies that can disperse *S. aureus* biofilms and kill biofilm-embedded *S. aureus* bacteria.

SUMMARY OF THE INVENTION

In one embodiment, the present invention provides a composition for preventing and/or inhibiting the growth of biofilm-embedded *S. aureus* bacteria comprising: (a) a first compound comprising a deoxyribonuclease, or an active fragment or variant thereof, that disperses a biofilm; and (b) a second compound comprising an antimicrobial agent that is active against *S. aureus* cells.

In another embodiment, the deoxyribonuclease enzyme is deoxyribonuclease I.

In another embodiment, the deoxyribonuclease enzyme is bovine deoxyribonuclease I.

In another embodiment, the deoxyribonuclease enzyme is human deoxyribonuclease I.

In yet another embodiment, the antimicrobial agent is the quaternary ammonium compound cetylpyridinium chloride, also known as hexadecylpyridinium chloride.

An embodiment of the invention includes a method for treating a *S. aureus* infection by administering a composition comprising (a) a deoxyribonuclease enzyme, or a deoxyribonuclease fragment or variant thereof; and (b) an antimicrobial agent or mixture of antimicrobial agents.

In yet another embodiment, the deoxyribonuclease-based antimicrobial composition of the invention can be used to treat various kinds of wounds, including, but not limited to, surgical wounds, accidental wounds, burn wounds, leg ulcers, foot ulcers, venous ulcers, diabetic ulcers, and pressure ulcers.

In yet another embodiment, the deoxyribonuclease-based antimicrobial composition of the invention can be used to eradicate *S. aureus* nasal carriage.

In yet another embodiment, the deoxyribonuclease-based antimicrobial composition of the invention can be used to treat ocular infections.

In yet another embodiment, the deoxyribonuclease-based antimicrobial composition of the invention can be used as an antiseptic rinse for use on skin, medical devices, surgical instruments, and the like, before, during or after invasive procedures such as catheter placement or surgery.

One aspect of the present invention includes providing methods of using the deoxyribonuclease-based antimicrobial composition of the invention in wound care devices, including, but not limited to, a spray applicator.

An additional aspect of the present invention includes wound care ointments, gels, and lotions comprising the deoxyribonuclease-based antimicrobial compositions of the invention, in addition to binders, wetting agents, adherents, thickeners, stabilizers, fillers, and the like.

DETAILED DESCRIPTION OF THE INVENTION

Figure 1:
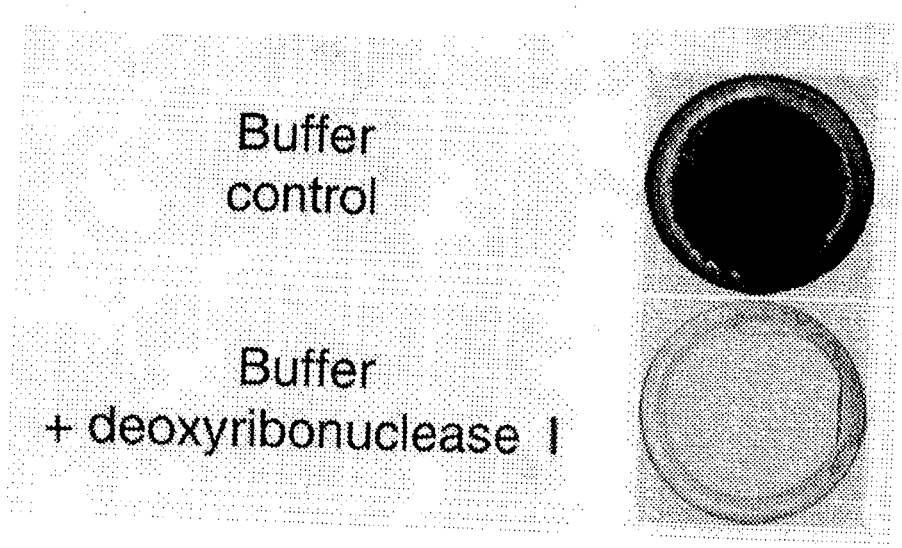
FIG. 1 shows that treatment of 24-h-old *S. aureus* biofilms grown in microtiter plate wells with a solution of 100 µg/ml of deoxyribonuclease I (10 min treatment) causes significant detachment of the biofilm, as judged by visual inspection of the amount of crystal violet staining material remaining in the well after treatment.

This invention relates to a method and composition for preventing and/or inhibiting the growth of biofilm-embedded *S. aureus* bacteria. The basis of the invention is the discovery that the bacteria is most susceptible when it is subject first to a means of detaching *S. aureus* biofilm and then is exposed to an agent which kills the bacteria.

It has been found that deoxyribonuclease enzyme or active fragment or variant thereof is capable of inhibiting *S. aureus* biofilm formation when added to a culture medium. Examples include human deoxyribonuclease I and bovine deoxyribonuclease I.

Agents which are capable of killing *S. aureus* are known in the art and include antimicrobial compounds such as quaternary ammonium salts. Examples of quaternary ammonium salts include for example, but not limited to, cetylpyridinium chloride, methacryloyloxydodecyl pyridinimium bromide, like pyridinium halide salts, benzalkoniumchloride, methacryloxylethylbenzyl dimethylammonium chloride and methacryloxylethylcetyldimethyl ammonium chloride.

The *S. aureus* can be treated by the administration of the deoxyribonuclease enzyme and the antimicrobialanat agent at the same time or serially with the deoxyribonuclease enzyme being administered before the antimicrobial agent.

Any pharmaceutically acceptable vehicle or carrier, as well as adjuvant, can be used in the manufacture, dissolution and administration of pharmaceutical preparations of the invention comprising deoxyribonuclease enzyme or active fragment or variant thereof and/or the antimicrobial agent. Such vehicles, carriers and adjuvants are well known to those of skill in the art and described in text books such as Remington's Pharmaceutical Sciences, Mack Publishing Co., Easton, Pa., 1985. Appropriate concentrations of active composition to be incorporated into pharmaceutical compositions can be routinely determined by those skilled in the art and is dependent upon the form of administration as well as the severity of the condition being treated.

Pharmaceutical formulations suitable for oral administration may be provided in convenient unit forms including, but not limited to, capsules or tablets, each containing a predetermined amount of the deoxyribonuclease enzyme or active fragment or variant thereof and/or the antimicrobial agent; as a powder or granules; as a solution, a suspension or as an emulsion. The deoxyribonuclease enzyme or active fragment or variant thereof and/or the antimicrobial agent can also be presented as a bolus, electuary, or paste. Tablets and capsules for oral administration may contain conventional excipients such as binding agents, fillers, lubricants, disintegrants, or wetting agents. The tablets may be coated according to methods well known in the art. Timed release formulations, which are known in the art, may also be suitable. Oral liquid preparations may be in the form of, for example, aqueous or oily suspensions, solutions, emulsions, syrups or elixirs, or may be presented as a dry product for constitution with water or other suitable vehicles before use. Such liquid preparations may contain conventional additives such as suspending agents, non-aqueous vehicles, including edible oils, or preservatives.

Deoxyribonuclease enzyme or active fragment or variant thereof and/or the antimicrobial agent of the present invention may also be formulated for parenteral administration, such as by injection, for example bolus injection or continuous infusion, and may be provided in unit dose form in ampules, pre-filled syringes, small volume infusion or in multi-dose containers with an added preservative. Pharmaceutically acceptable compositions comprising a deoxyribonuclease enzyme or active fragment or variant thereof and/or the antimicrobial agent for parenteral administration may be in the form of a suspension, solution or emulsion in oily or aqueous vehicles, and may contain formulatory agents such as suspending, stabilizing, and/or dispersing agents. Alternatively, the active ingredient may be in powder form, obtained by asceptic isolation of sterile solid or by lyophilization from solution, for constitution with a suitable vehicle such as sterile, pyrogen free water, before use.

For topical administration to the epidermis, deoxyribonuclease enzyme or active fragment or variant thereof and/or the antimicrobial agent of the present invention may be formulated in an ointment, cream, or lotion, or as a transdermal patch. Ointments and creams, may, for example, be formulated with an aqueous or oily base with the addition of suitable thickening and/or gelling agents. Lotions may be formulated with an aqueous or oily base and will in general also contain one or more emulsifying agents, stabilizing agents, suspending agents, thickening agents, or coloring agents. Formulations suitable for topical administration in the mouth include lozenges comprising deoxyribonuclease enzyme or active fragment or variant thereof and/or the antimicrobial agent in a flavored base, usually sucrose and acacia or tragacanth; pastilles comprising the active ingredient in an inert base such as gelatin and glycerin or sucrose and acacia; and mouth washes comprising the active ingredient in a suitable liquid carrier. For topical administration to the eye, the deoxyribonuclease enzyme or active fragment or variant thereof and/or the antimicrobial agent can be made up in solution or suspension in a suitable sterile aqueous or non-aqueous vehicle. Additives such as buffers (e.g. sodium metabisulphite or disodium edeate) and thickening agents such as hypromellose can also be included.

For intra-nasal administration, deoxyribonuclease enzyme or active fragment or variant thereof and/or the antimicrobial agent of the present invention can be provide in a liquid spray or dispersible powder or in the form of drops. Drops may be formulated with an aqueous or non-aqueous base also comprising one or more dispersing agents, solubilizing agents, or suspending agents. Liquid sprays are conveniently delivered from pressurized packs. For administration by inhalation, deoxyribonuclease enzyme or active fragment or variant thereof and/or the antimicrobial agent of the present invention can be delivered by insufflator, nebulizer or a pressurized pack or other convenient means of delivering the aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount.

Alternatively, for administration by inhalation or insufflation, the deoxyribonuclease enzyme or active fragment or variant thereof and/or the antimicrobial agent of the present invention can take the form of a dry powder composition, for example a powder mix of the active component and a suitable powder base such as lactose or starch. The powder composition may be presented in unit dosage form in, for example, capsules, cartridges or blister packs of gelatins, from which the powder can be administered with the aid of an inhalator or insufflator.

When desired, any of the above-described formulations may be adapted to provide sustained release of the deoxyribonuclease enzyme or active fragment or variant thereof and/or the antimicrobial agent.

The amount of deoxyribonuclease enzyme or active fragment or variant thereof and/or the antimicrobial agent of the present invention required for use in treatment will of course vary not only with the particular protein or active fragment or variant selected but also with the route of administration, the nature of the condition being treated, and the age and condition of the organism.

Increasing detachment of bacteria from a biofilm is also expected to decrease resistance of the bacteria to antibiotic therapy. Accordingly, the present invention also provide methods for enhancing efficacy of antibiotic therapy against bacterial infections by administration of a pharmaceutical composition of the present invention in combination with or prior to administration of an antibiotic.

In another embodiment of the present invention, wound dressings including but not limited to sponges or gauzes can be impregnated with the isolated deoxyribonuclease enzyme or active fragment or variant thereof and/or the antimicrobial agent thereof to prevent or inhibit bacterial or fungal attachment and reduce the risk of wound infections. Similarly, catheter shields as well as other materials used to cover a catheter insertion sites can be coated or impregnated with a deoxyribonuclease enzyme or active fragment or variant thereof and/or the antimicrobial agent to inhibit bacterial or fungal biofilm attachment thereto. Adhesive drapes used to prevent wound infection during high risk surgeries can be impregnated with the isolated protein or active fragment or variant thereof as well. Additional medical devices which can be coated with a deoxyribonuclease enzyme or active fragment or variant thereof and/or the antimicrobial agent thereof include, but are not limited, central venous catheters, intravascular catheters, urinary catheters, Hickman catheters, peritoneal dialysis catheters, endotracheal catheters, mechanical heart valves, cardiac pacemakers, arteriovenous shunts, schleral buckles, prosthetic joints, tympanostomy tubes, tracheostomy tubes, voice prosthetics, penile prosthetics, artificial urinary sphincters, synthetic pubovaginal slings, surgical sutures, bone anchors, bone screws, intraocular lenses, contact lenses, intrauterine devices, aortofemoral grafts and vascular grafts. Exemplary solutions for impregnating gauzes or sponges, catheter shields and adhesive drapes or coating catheter shields and other medical devices include, but are not limited to, phosphate buffered saline (pH approximately 7.5) and bicarbonate buffer (pH approximately 9.0).

In yet another embodiment, an isolated deoxyribonuclease enzyme or active fragment or variant thereof and/or the anatimicrobial agent can be incorporated in a liquid disinfecting solution. Such solutions may further comprise antimicrobials or antifungals such as alcohol, providone-iodine solution and antibiotics as well as preservatives. These solutions can be used, for example, as disinfectants of the skin or surrounding area prior to insertion or implantation of a device such as a catheter, as catheter lock and/or flush solutions, and as antiseptic rinses for any medical device including, but not limited to catheter components such as needles, Leur-Lok connectors, needleless connectors and hubs as well as other implantable devices. These solutions can also be used to coat or disinfect surgical instruments including, but not limited to, clamps, forceps, scissors, skin hooks, tubing, needles, retractors, scalers, drills, chisels, rasps and saws.

The compositions and method of the invention can be used for the treatment and prevention of wound and burn infections caused by *S. aureus* as well as other infections caused by *S. aureus* including boils and sties and bovine mastitis. The compositions can be used as a preprocedural rinse for surgery, as an antiseptic rinse, a topical antiseptic and a catheter lock solution.

The composition and method of the instant invention can also be used for the treatment and prevention of biofilm infections caused by other bacteria including otitis media, sinusitis and chronic obstructive pulmonary disease (*Haemophilus influenzae*), dental caries (*Streptococcus mutans*), acne (*Propionibacterium acnes*), and periodontitis (mixed-species biofilms).

EXAMPLES

Example 1

Deoxyribonuclease I Causes the Detachment and Dispersal of *S. aureus* Biofilms

*S. aureus* Strain SH1000 (Horsburgh et al., 2002. J. Bacteriol. 184:5457-5467) was used in all of the following examples. The bacteria were passaged weekly on blood agar and stored at 4° C. Biofilms were cultured in Tryptic Soy broth (Becton-Dickinson, Sparks, Md.) containing 6 g of yeast extract and 8 g of glucose per liter (TSB medium). All cultures were incubated at 37° C.

A biofilm formation assay was carried out as follows. A loopful of cells from an agar plate was transferred to a polypropylene microcentrifuge tube containing 200 µl of TSB medium. The cells were crushed with a disposable pellet pestle, vortexed for 30 sec, diluted to 1 ml in fresh TSB medium, and then passed through a 5-µm pore-size syringe filter to remove large clumps of cells as previously described (Kaplan & Fine, 2002. Appl. Environ. Microbiol. 68:4943-4950). Filtered cells were diluted to $10^3$-$10^5$ CFU/ml in TSB medium. Aliquots of cells (200 µl each) were transferred to the wells of a 96-well tissue-culture-treated polystyrene microtiter plate (Falcon no. 324662, Becton-Dickinson) and the plate was incubated for 24 h. The biofilms were rinsed once with water and then treated with 200 µl of deoxyribonuclease I (bovine deoxyribonuclease I, purchased from Sigma Chemical Company) at 100 µg/ml in 150 mM NaCl, 1 mM $CaCl_2$. Control biofilms were treated with 200 µl of 150 mM NaCl, 1 mM $CaCl_2$ alone. After 10 min at 37° C., biofilms were rinsed with water and then dried. Biofilms were stained for 1 min with 200 µl of Gram's crystal violet stain (catalog no. 23255960, Fisher Scientific, Fair Lawn, N.J.) and then rinsed with water and dried. Previous studies showed that crystal violet stains the bacterial biofilm biomass but not the polystyrene microplate substrate (O'Toole & Kolter, 1998. Mol. Microbiol. 28:449-462).

FIG. 1 shows that the deoxyribonuclease I solution caused the nearly complete detachment of the *S. aureus* biofilm from the microplate well surface, as judged by the amount of crystal violet staining material that remained in the well after treatment.

Figure 2:
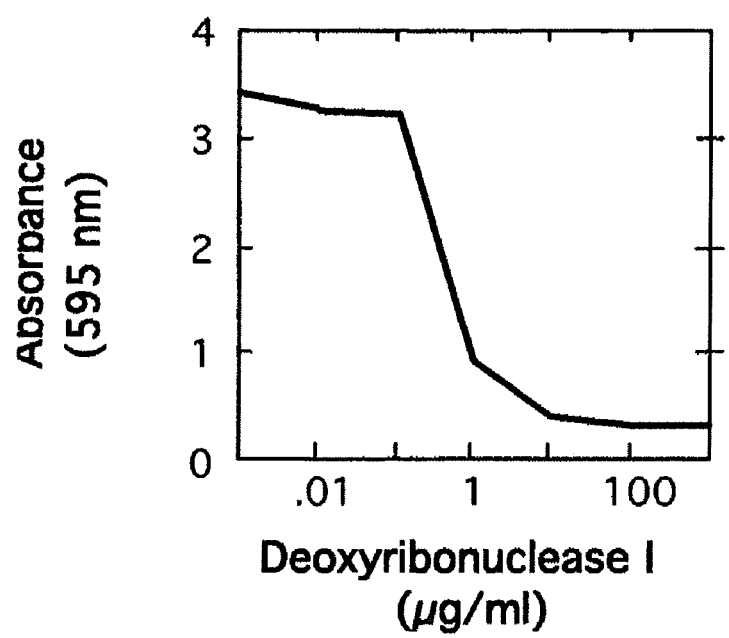
FIG. 2 shows that the detachment of 24-h-old *S. aureus* biofilms grown in microtiter plate wells by deoxyribonuclease I (10 min treatment) is dependent on the deoxyribonuclease I concentration, as judged by quantitation of the amount of crystal violet stain remaining in the well after treatment (Absorbance at 595 nm).

FIG. 2 shows the results of a similar experiment, except that increasing amounts of deoxyribonuclease I were used, and the amount of biofilm biomass remaining in the wells was quantitated by destaining the biofilms for 10 min with 33% acetic acid (by vol) and then measuring the absorbance of the crystal violet solution at 595 nm ($A_{595}$). Concentrations of deoxyribonuclease I that were less than 0.1 µg/ml caused little detachment of the biofilm. Concentrations of deoxyribonuclease I that were between 0.1 and 10 µg/ml caused partial detachment of the biofilm. Concentrations of deoxyribonuclease I that were greater than 10 µg/ml caused near complete detachment of the biofilm.

Figure 3:
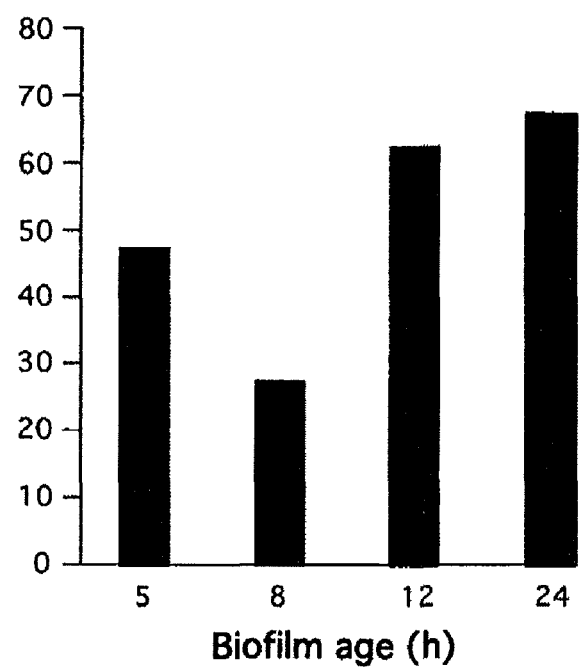
FIG. 3 shows that a solution of 100 µg/ml of deoxyribonuclease I (10 min treatment) is capable of detaching 5-h-old, 8-h-old, 12-h-old and 24-h-old *S. aureus* biofilms grown in microtiter plate wells.

FIG. 3 shows the results of a similar experiment, except that *S. aureus* biofilms that were grown for 5, 8, 12 or 24 h were used. The concentration of deoxyribonuclease I was 100 µg/ml and the treatment time was 10 min. In this case, the amount of biofilm biomass remaining in the well was quantitated by measuring the $A_{595}$ of the crystal violet stained biomass as described above, and the percent of biofilm cell detachment was calculated using the formula: $1-(A_{595}$ [buffer+deoxyribonuclease I]/$A_{595}$[buffer alone])×100. As can be seen in FIG. 3, the deoxyribonuclease I solution caused significant detachment of all of the *S. aureus* biofilms, regardless of their age.

Example 2

Deoxyribonuclease I Inhibits *S. aureus* Autoaggregation and Biofilm Formation

Figure 4:
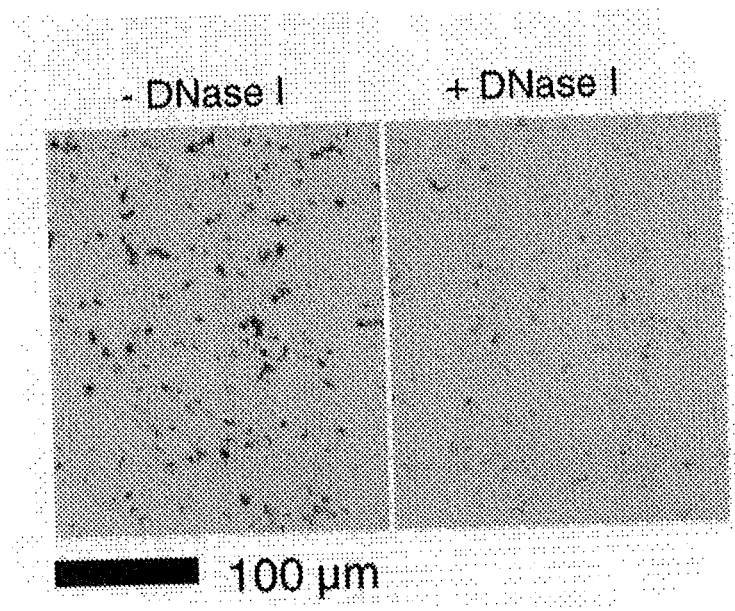
FIG. 4 shows that *S. aureus* cells grown in medium supplemented with 100 µg/ml of deoxyribonuclease I exhibit much less clumping (autoaggregation) than do cells grown in unsupplemented medium.
Figure 5:
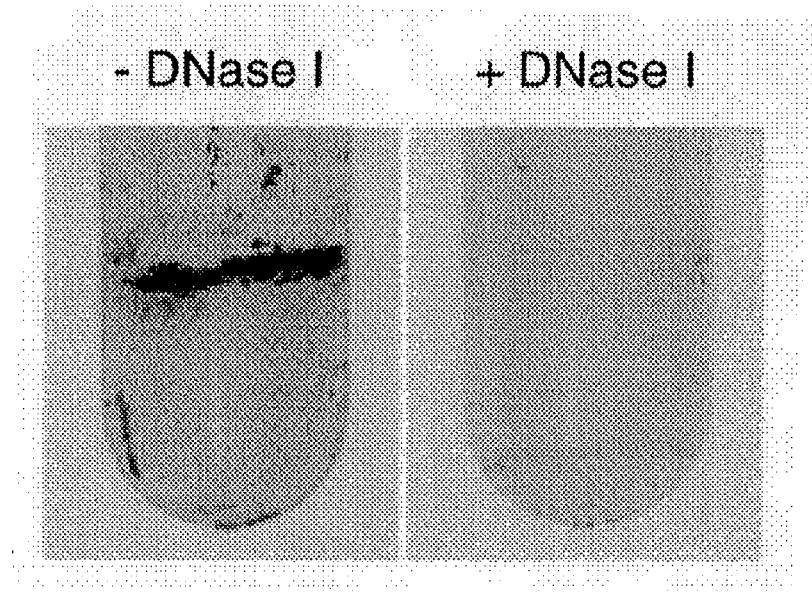
FIG. 5 shows that *S. aureus* cells grown in tubes in medium supplemented with 100 µg/ml of deoxyribonuclease I exhibit much less biofilm formation than do cells grown in unsupplemented medium.

A series of experiments was performed in order to demonstrate that deoxyribonuclease I inhibits *S. aureus* autoaggregation and biofilm formation. These experiments were carried out as described above, except that biofilms were grown in 16-mm×100-mm PET tubes (2 ml culture vol) in a rotary shaker for 16 h. FIG. 4 shows *S. aureus* SH1000 cells cultured in this manner in unsupplemented TSB medium formed large aggregates, whereas cells cultured in this manner in TSB medium supplemented with 100 µg/ml of deoxyribonuclease I formed smaller aggregates. Crystal violet staining of the culture tubes showed that deoxyribonuclease I inhibited biofilm formation at the air-liquid interface (FIG. 5).

Figure 6:
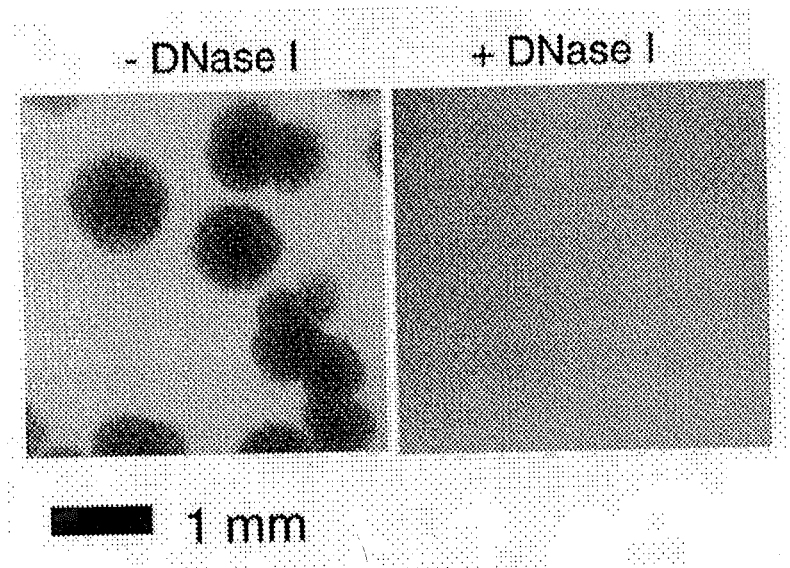
FIG. 6 shows that *S. aureus* cells grown in microplate wells in medium supplemented with 100 µg/ml of deoxyribonuclease I are incapable of forming distinct biofilm colonies.
Figure 7:
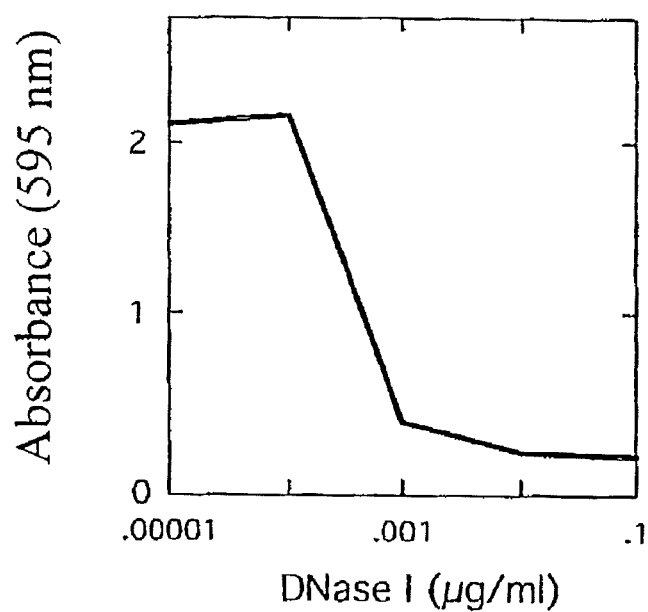
FIG. 7 shows that the inhibition of *S. aureus* biofilms grown in microtiter plate wells by deoxyribonuclease I is dependent on the deoxyribonuclease I concentration.

FIG. 6 shows that SH1000 biofilms grown for 24 h in 96-well microtiter plates in unsupplemented TSB medium formed distinct, spherical colonies that were tightly attached to the microwell surface, whereas biofilms grown in TSB medium supplemented with 100 µg/ml of deoxyribonuclease I formed a dense film that uniformly covered the microwell surface, but which readily detached after gentle rinsing. FIG. 7 shows that deoxyribonuclease I inhibited SH1000 biofilm formation in a dose-dependent manner, as determined by measuring the $A_{595}$ of the crystal violet stained biofilm biomass as described above.

Example 3

Deoxyribonuclease I Increases the Sensitivity of *S. aureus* Biofilm Cells to Killing by the Quaternary Ammonium Compound Cetylpyridinium Chloride (CPC)

Biofilms were grown for 24 h in 96-well microtiter plates as described above. Biofilms were rinsed once with water and then treated with 200 µl of TSB medium containing 100 µg/ml of deoxyribonuclease I. Control wells were treated with 200 µl of TSB medium alone. After 10 min at 37° C., 20 µl of 3% CPC was added to each well and biofilms were incubated for 5 min at room temperature. Control wells received 20 µl of water. For biofilms treated with TSB medium alone, biofilms were washed four times with phosphate buffered saline to remove the CPC, and then treated with 100 µg/ml of deoxyribonuclease I to dissolve the biofilm. This reaction was carried out in 100 µg/ml in 150 mM NaCl, 1 mM $CaCl_2$ as described above. After 10 min, cells were mixed and then serial dilutions were plated on agar. For *S. aureus* biofilms treated with deoxyribonuclease I, cells were mixed and then a 50-µl aliquot of cells was diluted in 50 ml of phosphate buffered saline. The cells were passed through an analytical test filter funnel (no. 145-2020; Nalgene, Rochester, N.Y.), and the filter was rinsed with 250 ml of sterile water, aseptically removed from the filter unit, and placed on a blood agar plate. Colonies were enumerated after 24 h.

Figure 8:
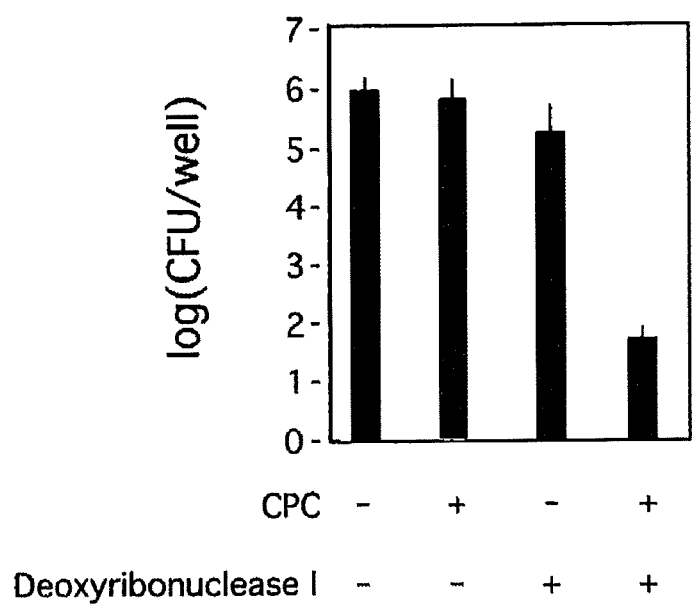
FIG. 8 shows that *S. aureus* biofilm cells grown in microplate wells are resistant to killing by 100 µg/ml of deoxyribonuclease I for 10 min, and by 0.3% cetylpyridinium chloride (CPC) for 5 min, but that treatment of the biofilms with 100 µg/ml of deoxyribonuclease I for 10 min followed by treatment with 0.3% CPC for 5 min results in significant killing of the biofilm cells.
Figure 9:
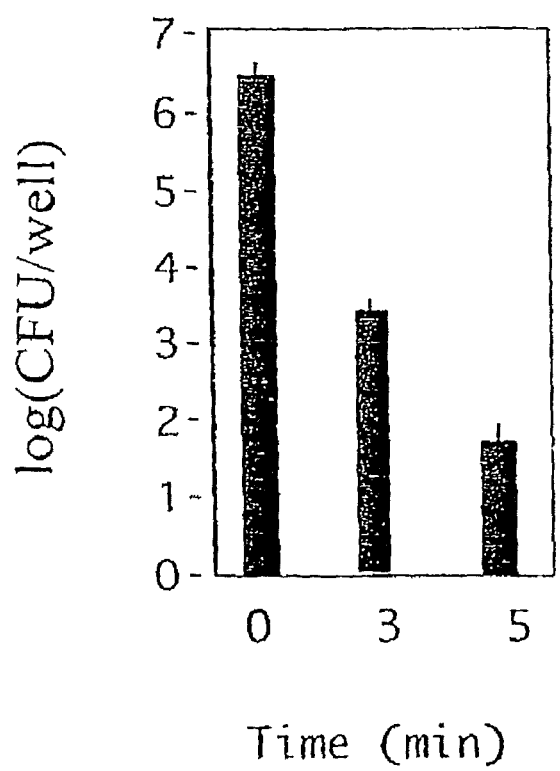
FIG. 9 shows that treatment of *S. aureus* biofilm cells grown in microplate wells with 100 µg/ml of deoxyribonuclease I for 10 min followed by treatment with 0.3% CPC for 3 min or 5 min results in significant killing of the biofilm cells.

As can be seen in FIG. 8, *S. aureus* biofilms treated with either deoxyribonuclease I alone or CPC alone did not exhibit a significant decrease in CFU/well values, whereas *S. aureus* biofilms treated with deoxyribonuclease I followed by CPC exhibited an approximately 4-log-unit decrease in CFU/well values. A significant decrease in the CFU/well values was also observed after a 10 min deoxyribonuclease I treatment followed by a 3 min CPC treatment (FIG. 9).

What is claimed is:

1. A method for increasing sensitivity of *S. aureus* biofilm-embedded cells to killing, said method comprising treating the *S. aureus* biofilm-embedded cells with a deoxyribonuclease enzyme, wherein the antimicrobial agent or the mixture of antimicrobial agents is active against *S. aureus* cells followed by treatment of the deoxyribonuclease enzyme treated cells with an antimicrobial agent or mixture of antimicrobial agents.

2. The method of claim 1 wherein the deoxyribonuclease enzyme is deoxyribonuclease I.

3. The method of claim 1 wherein the deoxyribonuclease enzyme is bovine deoxyribonuclease I.

4. The method of claim 1 wherein the deoxyribonuclease enzyme is human deoxyribonuclease I.

5. The method of claim 1 wherein the antimicrobial agent is a quaternary ammonium compound.

6. The method of claim 5 wherein the quaternary ammonium compound is cetylpyridinium chloride.

7. The method of claim 1 wherein the cells are treated with the deoxyribonuclease enzyme for at least 10 minutes.

8. The method of claim 7 wherein the cells are treated with the antimicrobial agent or mixture thereof for at least 3 minutes.

9. The method of claim 1 wherein the cells are treated with at least 100 µg/ml of the deoxyribonuclease enzyme.

\* \* \* \* \*

UNITED STATES PATENT AND TRADEMARK OFFICE
CERTIFICATE OF CORRECTION

| | | |
|---|---|---|
| PATENT NO. | : 8,765,123 B1 | Page 1 of 1 |
| APPLICATION NO. | : 13/609714 | |
| DATED | : July 1, 2014 | |
| INVENTOR(S) | : Jeffrey B. Kaplan | |

It is certified that error appears in the above-identified patent and that said Letters Patent is hereby corrected as shown below:

In the Claims

Column 10, lines 5-6, claim 1, delete ", wherein the antimicrobial agent or the mixture of antimicrobial agents is active against *S. aureus* cells"

Column 10, line 9, claim 1, add after "agents" --, wherein the antimicrobial agent or the mixture of antimicrobial agents is active against *S. aureus* cells--

Signed and Sealed this
Ninth Day of September, 2014

Michelle K. Lee
*Deputy Director of the United States Patent and Trademark Office*